(12) United States Patent
Lange et al.

(10) Patent No.: US 7,666,396 B2
(45) Date of Patent: Feb. 23, 2010

(54) SINGLE-USE MOISTURIZING PRODUCT

(75) Inventors: Beth A. Lange, Neenah, WI (US);
Duane Krzysik, Appleton, WI (US);
Jennifer Marvin, Greenville, WI (US);
Mike Brunner, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 740 days.

(21) Appl. No.: 10/659,970

(22) Filed: Sep. 11, 2003

(65) Prior Publication Data

US 2005/0058613 A1    Mar. 17, 2005

(51) Int. Cl.
*A61Q 1/02* (2006.01)
*A61Q 1/04* (2006.01)
*A61K 8/02* (2006.01)
*A61K 9/14* (2006.01)

(52) U.S. Cl. .................. 424/63; 424/64; 424/401; 424/484; 424/485; 424/486; 424/487; 424/488

(58) Field of Classification Search .................. 424/401, 424/484–488, 63–64
See application file for complete search history.

(56) References Cited

U.S. PATENT DOCUMENTS

| | | | |
|---|---|---|---|
| 3,803,300 A | 4/1974 | Pospischil | |
| 4,713,243 A | 12/1987 | Schiraldi et al. | |
| 4,724,240 A | 2/1988 | Abrutyn | |
| 4,795,631 A | 1/1989 | Sheehan | |
| 5,069,232 A | 12/1991 | Staar | |
| 5,462,737 A | 10/1995 | Pfleuger | |
| 5,466,251 A | 11/1995 | Brunson et al. | |
| 5,576,364 A | 11/1996 | Isaac et al. | |
| 5,629,003 A | 5/1997 | Horstmann et al. | |
| 5,747,017 A | 5/1998 | Nichols et al. | |
| 5,780,047 A * | 7/1998 | Kamiya et al. | 424/443 |
| 5,785,905 A | 7/1998 | Sheffler et al. | |
| 5,876,736 A | 3/1999 | Cohen et al. | |
| 5,908,631 A | 6/1999 | Arnaud et al. | |
| 5,938,435 A | 8/1999 | Raspino, Jr. | |
| 6,001,374 A | 12/1999 | Nichols | |
| 6,006,916 A | 12/1999 | Matsos et al. | |
| 6,015,513 A | 1/2000 | Sheffler et al. | |
| 6,035,867 A | 3/2000 | Barrick | |
| 6,395,263 B1 | 5/2002 | Nichols et al. | |
| 6,406,683 B1 | 6/2002 | Drechsler et al. | |
| 6,419,903 B1 | 7/2002 | Xu et al. | |
| 6,436,020 B1 | 8/2002 | Weingand | |
| 6,497,887 B1 | 12/2002 | Zecchino et al. | |
| 6,528,073 B2 | 3/2003 | Roulier et al. | |
| 6,555,097 B1 | 4/2003 | Rabe et al. | |
| 6,592,887 B2 | 7/2003 | Zerbe et al. | |
| 6,596,298 B2 | 7/2003 | Leung et al. | |
| 6,800,329 B2 * | 10/2004 | Horstmann et al. | 427/379 |
| 2002/0081321 A1 * | 6/2002 | Konno et al. | 424/401 |
| 2002/0197221 A1 | 12/2002 | Nichols et al. | |
| 2003/0068344 A1 | 4/2003 | Ferrari et al. | |
| 2003/0082221 A1 * | 5/2003 | O'Halloran et al. | 424/401 |
| 2003/0086954 A1 * | 5/2003 | O'Halloran et al. | 424/401 |
| 2003/0099691 A1 | 5/2003 | Lydzinski et al. | |
| 2003/0099692 A1 | 5/2003 | Lydzinski et al. | |
| 2004/0071755 A1 * | 4/2004 | Fox | 424/443 |

FOREIGN PATENT DOCUMENTS

| | | | |
|---|---|---|---|
| EP | 0 471 558 A2 | | 2/1992 |
| EP | 1 136 057 A1 | | 9/2001 |
| EP | 1 454 950 A1 | | 9/2004 |
| FR | 851 701 A | | 1/1940 |
| FR | 2 503 561 A | | 10/1982 |
| JP | 61176512 A | * | 8/1986 |
| JP | 02042011 A | * | 2/1990 |
| JP | 11060443 A | * | 3/1999 |
| JP | 11 209222 A | | 8/1999 |
| JP | 11209222 A | * | 8/1999 |
| WO | WO 00/18365 A2 | | 4/2000 |
| WO | WO 03/003957 A1 | | 1/2003 |
| WO | WO 03030881 A1 | * | 4/2003 |

OTHER PUBLICATIONS

International Search Report from PCT/US2004/011042 dated Oct. 25, 2004.

* cited by examiner

*Primary Examiner*—Sreeni Padmanabhan
*Assistant Examiner*—Renee Claytor
(74) *Attorney, Agent, or Firm*—Armstrong Teasdale LLP

(57) ABSTRACT

A single-use lip treatment product is disclosed. The single-use lip treatment product comprises a moisturizer and dissolves rapidly when applied to the lips providing a moisturizing benefit to the lips.

26 Claims, No Drawings

SINGLE-USE MOISTURIZING PRODUCT

BACKGROUND OF THE INVENTION

The present invention relates to a single-use moisturizing product comprising a dissolvable film. More particularly, the present invention relates to dissolvable lip moisturizing films comprising a moisturizing agent that substantially dissolve when in contact with the lips. The lip moisturizing films can be individually dispensed from a multi-pack of films and introduced onto the lips where the lip moisturizing film substantially dissolves in a short period of time to provide a moisturizing benefit to the lips.

The lips are one of the most sensitive areas of the human body. As such, it is commonplace for the lips to become dry and chapped, or otherwise damaged from, for example, sun exposure, wind exposure, exposure to hot food and liquids, and other environmental factors. Severely dry lips can require preventative measures and continuing treatment to restore them to their natural, healthy state. Without such treatment, lips can become so dry and abraded as to crack and peel, which can result in inflammation and even infection. Additionally, in such a cracked and peeled state, the lips are very tender and sensitive, and can become very uncomfortable.

Because of the sensitive nature of lips, it is commonplace for many individuals to consistently treat lips with protective agents, moisturizing agents, and the like in an attempt to protect their lips from various environmental factors. However, lip treatment agents in the form of a stick, tube, or tub cannot readily be shared between users without a significant risk of cross-contamination by bacteria, funguses, viruses, and other undesirable elements. Further, it is routine for the lip treatment agent device to become dirty or contaminated with environmental agents such as dust, dirt, and the like after several uses, which significantly increases the risk of introducing unwanted elements onto the lips during application. The introduction of dust or dirt onto the lips during an application of a lip treatment agent can actually cause increased stress on the lips and result in a deteriorating condition of the lips.

Additionally, persons with transmittable diseases, such as herpes virus, related viruses, and the like, need to be especially careful not to contaminate their personal lip treatment products in order not to reintroduce the virus during subsequent applications. As such, during even a minor outbreak, it is necessary for a user to replace the lip treatment agent after only a single-use to ensure that later contamination does not occur after treatment of the lips.

Based on the foregoing, there is a need in the industry for a single-use lip treatment product that eliminates the potential for cross-contamination between users, and eliminates the potential for the re-contamination of a single user with a viral or other harmful agent. Preferably, the lip treatment agent would comprise a lip moisturizing agent for treating severely dry lips, and be easily dispensable.

SUMMARY OF THE INVENTION

The single-use lip moisturizing products described herein provide a hygienic method for applying a lip treatment agent, such as a lip moisturizing agent, to the lips. Generally, the single-use lip treatment product is sized and configured to approximately match the average consumer's lips, and is generally oval in shape. The single-use lip treatment products are generally stretchable to allow for custom fitting to the user's lips as well as for providing a comfortable product for use.

Specifically, the present invention relates to a single-use lip treatment product. The single-use lip treatment product is a self-adhering, stretchable, dissolvable film that is placed on moistened lips such that it substantially dissolves upon contact due to moisture, temperature, and pressure, thus providing a topical application and protection. In one embodiment, the single-use lip treatment product comprises a moisturizing agent, such as glycerin or petrolatum, that is transferred to the lips upon the dissolution of the product onto the lips.

Along with single-use lip moisturizing products, the present invention additionally includes single-use moisturizing products for use on the face and body. In particular, the single-use moisturizing products comprise a dissolvable film, which comprises a moisturizing agent, and may include products such as moisturizing strips for the face, dry elbow moisturizing pads and other related pads.

In another embodiment, the single-use treatment products comprising a moisturizing agent additionally include another treatment agent, such as a sunscreen agent, a botanical agent, a skin protectant, an essential oil agent, an antimicrobial, a pharmaceutically active agent and the like to introduce multiple benefits simultaneously to the user.

Specifically, the present invention is directed to a single-use lip treatment product. The product comprises from about 0.01% (by weight) to about 99.9% (by weight) of a water-soluble film forming polymeric material, from about 0.01% (by weight) to about 50% (by weight) of a moisturizing agent, and from about 0.1% (by weight) to about 50% (by weight) of a solidifying agent. The single-use lip treatment product is a film, and comprises a single layer. Further, the single-use lip treatment product is sized and configured for application to the lips.

The present invention is further directed to a dissolvable lip moisturizing product. The product comprises from about 0.01% (by weight) to about 99.9% (by weight) of pullulan, from about 0.01% (by weight) to about 50% (by weight) of glycerin, and from about 0.1% (by weight) to about 50% (by weight) of a solidifying agent. Further, the single-use lip treatment product is sized and configured for application to the lips.

The present invention is further directed to a single-use lip treatment product. The product comprises from about 0.01% (by weight) to about 99.9% (by weight) of a water-soluble film forming polymeric material, from about 0.01% (by weight) to about 50% (by weight) of a moisturizing agent, and from about 0.1% (by weight) to about 50% (by weight) of a solidifying agent. The single-use lip treatment product is a film, and comprises a single layer. Further, the single-use lip treatment product is sized and configured for application to the lips.

Other features and advantages of this invention will be in part apparent and in part pointed out hereinafter.

DETAILED DESCRIPTION OF THE PREFERRED EMBODIMENTS

In accordance with the present invention, it has been discovered that single-use lip treatment products comprising a physiologically acceptable thin film including a moisturizing agent can be manufactured such that they readily substantially dissolve upon application to the lips due to the moisture and temperature thereon. As such, the single-use lip treatment product is an effective, hygienic product for treating and moisturizing the lips. The dissolving films of the present invention, which can also include a number of optional components, can be conveniently dispensed individually from a multi-pack as needed without risk of cross-contamination between multiple users, and without risk of re-contamination of a single user. Additionally, the dissolvable films comprising a moisturizing agent may be applied to other areas of the face or body to impart a moisturizing benefit thereto.

The single-use lip treatment products of the present invention are manufactured as described herein such that they have a resulting thickness which allows the single-use lip treatment product to have the required product integrity, yet readily substantially dissolve upon application to the lips due to the moisture content of the lips and temperature of the lips. Additionally, the user can apply pressure to the film by pressing their lips together to speed up the dissolution of the single-use lip treatment product.

Generally, a suitable thickness of the lip treatment product is from about 15 micrometers to about 80 micrometers, desirably from about 30 micrometers to about 60 micrometers. Within these ranges, the single-use lip treatment product readily substantially dissolves in a suitable amount of time. As one skilled in the art will recognize based on the disclosure herein, a thicker lip treatment product will typically take longer to dissolve on the lips, but will also typically be capable of providing more of a moisturizing benefit, along with other potential benefits as noted herein. Further, the actual lip treatment product thickness will depend upon numerous factors, including the polymeric film forming material utilized, as well as the actual beneficial components added to the lip treatment product.

The single-use lip treatment product has a rate of dissolution once applied to the lips such that the product substantially dissolves in an amount of time short enough to be satisfactory to consumers. Desirably, the single-use lip treatment products described herein will substantially dissolve on the lips after application thereto in an amount of time of no greater than about 50 seconds, more preferably no greater than about 20 seconds, more preferably no greater than about 15 seconds, and still more preferably no greater than about 10 seconds.

The single-use lip treatment products described herein are desirably sized and configured to conform to human lips. As noted above, the single-use lip treatment products are desirably stretchable to some degree to allow the consumer to custom fit the length and width of the single-use lip treatment product to his or her own lips. The flexural stiffness of the single-use lip treatment product is desirably such that the product will not lead to irritation of the lips of the user, even after multiple applications. Generally, the single-use lip treatment product is no more than about 8.0 centimeters in length, and may be about 3.0 centimeters in length to no more than about 8.0 centimeters in length, desirably about 4 centimeters in length.

The shape of the single-use lip treatment product is not critical, and may be any commercially desirably shape. In one embodiment, the single-use lip treatment product is oval in shape to conform the user's lips. However, the single-use lip treatment product need not be symmetrical, but desirably has rounded corners to comfortably fit the user. Additionally, the single-use lip treatment product may comprise slits, holes or other perforations depending upon the desired embodiment and application.

Single-Use Lip or Body Treatment Product Composition

The single-use lip or body treatment products described herein are comprised of a water-soluble and/or water-dispersible film forming polymeric material, a moisturizing agent, and a solidifying agent. Desirably, the single-use lip or body treatment product is a single layer product, which substantially dissolves in a short time upon application to the user's lips or body. In a less preferred embodiment, the single-use lip or body treatment product may be comprised of multiple layers stacked one on top of the other. In this embodiment, each layer may comprise a separate beneficial ingredient.

The water-soluble and/or water-dispersible film forming polymeric material, which provides the structural integrity of the product, is present in the single-use lip or body treatment product in an amount of from about 0.01% (by weight) to about 99% (by weight), desirably from about 40% (by weight) to about 70% (by weight), and more desirably from about 60% (by weight) to about 65% (by weight).

Suitable water-soluble film forming polymeric materials include, but are not limited to, starch, pullulan, hydroxypropylmethyl cellulose, hydroxyethyl cellulose, hydroxypropyl cellulose, polyvinyl pyrrolidone, carboxymethylcellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, nigeran, collagen, gelatin, zein, gluten, soy protein isolate, whey protein isolate, casein and mixtures thereof. Particularly preferred water-soluble film forming polymeric materials include pullulan and starch.

As noted above, the film forming polymeric material may be water-dispersible; that is, the film may be capable of forming a dispersion in an aqueous medium at ambient temperature instead of dissolving in the aqueous medium. While any suitable water-dispersible polymeric may be utilized in manufacturing the single-use lip treatment products described herein, exemplary water-dispersible polymers include such polymers chosen from the group including relatively high molecular weight amorphous polyesters that disperse directly in water without the assistance of organic cosolvents, surfactants, or amines. This water dispersibility is attributable, in large part, to the presence of ionic substituents attached to the polymer chain as illustrated below:

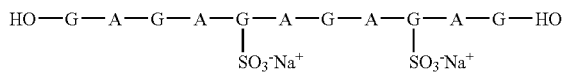

wherein A is an aromatic dicarboxylic acid moiety, G is an aliphatic or cycloaliphatic glycol residue and —OH are hydroxy end groups. While only two of the aromatic dicarboxylic acid moieties shown above have sodiosulfo ($SO_3^-$ $Na^+$) substituents, on the average there are five to eight ionic sodiosulfo substituents per molecule.

This type of polymer is available from the Eastman Kodak Company (Rochester, N.Y.) under the trade name designation Eastman AQ. In particular, Eastman AQ 55D and AQ 38D. The "D" represents the fact that the polymer is in a dispersed form. The number refers to the dry glass transition temperature, in degrees Centigrade, of the polymer.

Alternatively, the water-dispersible polymer may be selected from the group including acrylic polymers, polyoxides, vinyl polymers, cellulose derivatives, starch derivatives, polysaccharides, proteins, and copolymers thereof.

In one embodiment, the single-use lip treatment product may comprise a combination of water-soluble and water-dispersible film forming polymeric materials in combination with the other components described herein. In this embodiment, a single-use lip treatment product is manufactured with improved integrity and strength as compared to a single-use lip treatment product solely comprising a water-soluble film forming polymeric material. Such improved integrity and strength may be desirable in some embodiments.

When the single-use lip or body treatment product is produced with a combination of water-soluble and water-dispersible film forming polymeric materials, the product comprises from about 0.01% (by weight) to about 99% (by weight), desirably from about 40% (by weight) to about 70% (by weight), and more desirably from about 60% (by weight) to about 65% (by weight) of the combination of film forming polymeric materials. Typically, the water-soluble film forming polymeric materials and the water-dispersible film forming polymeric materials are utilized in a ratio of about 1:10 to about 10:1 to produce the single-use lip or body treatment product.

In addition to the water-soluble or water-dispersible film forming polymeric material, the single-use lip and body treatment products comprise at least one moisturizing agent to impart a moisturization benefit upon the lips or body upon dissolution of the product. There are two main mechanisms that may be utilized to impart moisturization upon the lips or body; humectancy and occlusivity. Both of these mechanisms are suitable for use in the present invention for imparting a moisturizing benefit to the lips or body.

The occlusive approach includes the use of compositions, which are applied to the lips or body, that are capable of enhancing the ability of the lips or body to limit the loss of water vapor to the environment. The composition forms an occlusive or semi-occlusive film on the surface of the lips or body that results in the accumulation of water underneath the film which leads to an increase in lip or body hydration levels, and therefore reduces dryness. As used herein, the term "occlusive" is intended to include both occlusive and semi-occlusive moisturizing agents.

The humectancy approach utilizes hygroscopic materials that are capable of absorbing and holding water next to the lips or body. By increasing the ability of the lips or body to hold water on their surface, the humectant material provides a moisturizing benefit.

The single-use lip or body treatment products include from about 0.01% (by weight) to about 50% (by weight), desirably from about 1% (by weight) to about 25% (by weight) of a humectant, occlusive or semi-occlusive moisturizing agent to impart a moisturizing benefit to the lips or body upon use. Suitable humectant-type moisturizing agents include, but are not limited to, N-Acetyl ethanolamine, aloe vera gel, arginine PCA, chitosan PCA, copper PCA, Corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, urea, xylitol, panthenol, and mixtures thereof. A preferred humectant-type moisturizing agent is glycerin.

Suitable occlusive or semi-occlusive moisturizing agents include, but are not limited to, petrolatum, mineral oil, lanolin, lanolin alcohol, tocopherol, esters of tocopherol, alkyl polydimethylsiloxanes, vegetable oils, hydrogenated vegetable oils, fatty acid esters, beeswax, and the like. A preferred occlusive moisturizing agent is petrolatum.

The single-use lip or body treatment products include a solidifying agent in an amount suitable to help solidify the product at or near room temperature. Typically, the single-use lip or body treatment product will include from about 0.1% (by weight) to about 50% (by weight) solidifying agent, and desirably from about 1% (by weight) to about 10% (by weight) solidifying agent. Suitable solidifying agents include, but are not limited to, animal waxes, vegetable waxes, mineral waxes, synthetic waxes, bayberry wax, beeswax, $C_{30}$ alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, synthetic jojoba wax, metal soaps, solid polyethylene glycols, solid fatty acid esters, fatty alcohols, fatty acids copolymers or polymeric blends consisting of ethylene, propylene, butylene, styrene, or vinyl acetate, and combinations thereof.

Additionally, the single-use lip or body treatment products described herein may include other optional ingredients to impart other benefits or attributes to the products. For example, the single-use lip treatment product may include a flavor agent to enhance consumer appeal. Suitable flavor agents include both natural and artificial flavors. Flavor agents may include synthetic flavor oils and flavor aromatics and/or oils, oleo resins and extracts derived from plants, leaves, flowers, fruits, and so forth, and combinations thereof. Representative flavor oils include spearmint oil, cinnamon oil, peppermint oil, clove oil, bay oil, thyme oil, rosemary oil, cedar leaf oil, oil of nutmeg, oil of sage, and oil of bitter almonds. Other commonly used flavors include mints such as peppermint, artificial vanilla, cinnamon derivatives, and various fruit flavors. The amount of flavor agent included in the product is normally a matter of preference subject to such factors as flavor type, individual flavor, and strength desired. Typically, the flavor agent is present in an amount of from about 2% (by weight) to about 10% (by weight).

Another optional component which may be included in the single-use lip products described herein includes sweeteners. Suitable sweeteners include both natural and artificial sweeteners. Specifically, sweeteners such as water-soluble sweetening agents such as monosaccharides, disaccharides, and polysaccharides such as xylose, ribose, glucose (dextrose), mannose, galactose, fructose (levulose), sucrose, maltose, and water-soluble artificial sweeteners such as soluble saccharin salts are suitable for inclusion in the single-use lip products of the present invention. Typically, the sweetener is included in an amount of from about 0.01% (by weight) to about 2% (by weight).

Another optional component which may be included in the single-use lip or body products includes coloring agents. Suitable coloring agents include natural food colors and dyes suitable for food, drug and cosmetic applications. These coloring agents are sometimes referred to as FD&C dyes and lakes. Specifically, suitable materials are water-soluble and include FD&C Blue No. 2, which is the disodium salt of 5,5-indigotindisulfonic acid. Similarly, the dye known as Green No. 3 comprises a 15 triphenylmethane dye and is the monosodium salt of 4-[4-N-ethyl-p-sulfobenzylamino diphenyl-methylene]-[1-N-ethyl 1-N-sulfonium benzyl-2,5-cyclohexadienimine]. A full recitation of all FD&C and D&C dyes and their corresponding chemical structures may be found in the Kirk-Othrner Encyclopedia of Chemical Technology, Volume 5, Pages 857-884, which text is accordingly incorporated herein by reference.

Another optional component that may be included in the single-use lip or body treatment products described herein is an essential oil. An essential oil may provide some antimicrobial benefits when included in the single-use lip or body treatment products. Essential oils such as thymol, methyl salicylate, eucalyptol, and menthol are suitable for inclusion in the single-use lip treatment products. Typically, an essential oil will be included in an amount of from about 0.01% (by weight) to about 4.0% (by weight), desirably from about 0.5% (by weight) to about 3.0% (by weight).

Another optional ingredient that can be included in the single-use lip or body treatment product is an antimicrobial agent. Antimicrobial agents are capable of killing or controlling the growth of unwanted organisms. Suitable antimicrobial agents include, for example, triclosan, cetyl pyridium chloride, domiphen bromide, quaternary ammonium salts, zinc compounds, sanguinarine, fluorides, alexidine, octonidine, EDTA, and the like.

Some other optional ingredients include, for example, water, botanicals, coloring agents, lipids, pharmaceutically acceptable agents, skin protectants, Vitamin E, sunscreens, surfactants, and emulsifying agents.

As noted above, the present invention also includes single-use moisturizing strips for use on the face and body. These moisturizing strips are prepared as described herein, and may be applied to any area of the body that needs moisturizing. For example, in one embodiment the single-use face or body film or strip comprising a moisturizing agent may be applied to the elbow or knee area to provide moisturizing to the skin in this area. To ensure that the product dissolves in an acceptable amount of time to impart the desired benefit, the area to be treated is typically pre-moistened with water to improve the dissolution rate of the product onto the skin.

In another embodiment of the present invention, the single-use lip treatment products can comprise moisturizing and/or other active agents which are encapsulated or entrapped within a thin layer of material. The moisturizing and/or active agent can be encapsulated in a number of shell-like materials including, for example, liposomes, nanosomes, nanoparticles, collagen, gelatin, dextrin, melamine resin, silicon resin, starch, and combinations thereof. Alternatively, the encapsulating material may comprise a natural or synthetic polymer system (microsponge) such as, for example, acrylate polymers, acrylate copolymers, starch, silica, oat, and combinations thereof.

Encapsulating the moisturizing agent and/or active agent can protect the moisturizing and/or active agent from exposure to harsh environmental conditions which may result in premature oxidation and degradation of the product active ingredients and the overall product. Encapsulation also allows for the separation of any incompatible components within the product, which allows greater flexibility in the components which can be used to make the product. Additionally, encapsulation allows for a controlled release of the active ingredients during application of the lip film, or after the lip film has dissolved/dispersed on the lips of the wearer. A controlled release may include a triggered release, sustained release, or a combination of these release mechanisms, wherein the active ingredient is released from the encapsulant by a number of mechanisms including, for example, pressure, pH, ultraviolet light, capillary forces, and wetting with water or saliva.

Typically, the particle size of the microencapsulated materials and the polymeric entrapment materials are from about 0.1 micrometers to about 40 micrometers, desirably from about 0.3 micrometers to about 20 micrometers, and still more desirably from about 0.5 micrometers to about 15 micrometers.

Methods for Preparing Single-Use Lip and Body Treatment Product

Film Forming Polymer, Solidifying Agent and Moisturizing Agent All Substantially Water-Soluble When all of the components of the single-use lip or body treatment products of the present invention are substantially water-soluble, the product can be manufactured by introducing the water-soluble film forming polymeric material, solidifying agent and moisturizing agent (and any other substantially water-soluble optional ingredients) into deionized water. The deionized water may be heated to a temperature of from about 25° C. to about 50° C. to improve dissolution rate. Once introduced into the deionized water, the components are thoroughly mixed and allowed to hydrate and swell in the water for a period of from about 24 hours to about 48 hours, to form a gel-like material. The amount of water utilized to prepare the gel-like material is not critical, and is typically sufficient to produce a gel comprising from about 40% (by weight) to about 80% (by weight) water. The resulting gel-like material is chilled to a temperature of from about 20° C. to about 30° C. for from about 1 hour to about 48 hours.

After the gel-like material has been chilled for a sufficient period, the resulting gel mixture is cast onto a suitable substrate and dried. The substrate should have a surface tension that allows the resulting gel mixture to spread evenly across the substrate without the formation of a destructive bond between the mixture and the substrate. Suitable substrates include glass, stainless steel, Teflon, and polyethylene-impregnated paper. Drying of the mixture may be carried out at high temperatures using a drying oven, drying terminal, vacuum drier, or any other suitable drying equipment which does not adversely affect the components of the mixture. The resulting film may comprise up to about 10% moisture. The dried film is then segmented into individual units by die-cutting or slitting and die-cutting.

Film Forming Polymer, Moisturizing Agent and/or Stabilizing Agent not Substantially Water-Soluble When one of more of the components of the single-use lip treatment products of the present invention are not substantially water-soluble, the product can be manufactured by first introducing any substantially water-soluble components into deionized water. The deionized water may be heated to a temperature of from about 25° C. to about 50° C. to improve dissolution rate. Once introduced into the deionized water, the component(s) are thoroughly mixed and allowed to hydrate and swell in the water for a period of from about 24 hours to about 48 hours, to form a gel-like material. The amount of water utilized to prepare the gel-like material is not critical, and is typically sufficient to produce a gel comprising from about 40% (by weight) to about 80% (by weight) water. The resulting gel-like material is chilled to a temperature of from about 20° C. to about 30° C. for from about 1 hour to about 48 hours.

While the gel-like material described above is chilling, a second mixture comprising the substantially water-insoluble components, which may be all components in some embodiments, is prepared by introducing these components into water along with a suitable surfactant or emulsifying agent and thoroughly mixing these components to prepare an emulsified composition. The mixing may typically take from a few minutes to a few hours. Once the mixing is complete, the resulting emulsified mixture is mixed together with the chilled gel, if any, and the resulting mixture thoroughly mixed together for a period of from about 1 hour to about 24 hours to produce a substantially homogeneous mixture which is subsequently cast onto a suitable substrate and dried. The substrate should have a surface tension which allows the resulting mixture to spread evenly across the substrate without the formation of a destructive bond between the mixture and the substrate. Suitable substrates include glass, stainless steel, Teflon, and polyethylene-impregnated paper. Drying of the mixture may be carried out at high temperatures using a drying oven, drying terminal, vacuum drier, or any other suitable drying equipment which does not adversely affect the components of the mixture. The resulting film may comprise up to about 10% moisture. The dried film is then segmented into individual units by die-cutting or slitting and die-cutting.

In an alternative method, the single-use lip treatment product can be manufactured as described above with the exception that the moisturizing agent is not introduced as a raw component during the film manufacturing process, but is instead introduced onto the film once it is formed and dried. In this embodiment, the moisturizing agent, such as glycerin, is introduced onto the dried, formed dissolvable film in the last step of the manufacturing process.

In view of the above, it will be seen that the several objects of the invention are achieved. As various changes could be made in the above-described products and methods without departing from the scope of the invention, it is intended that all matter contained in the above description be interpreted as illustrative and not in a limiting sense.

What is claimed is:

1. A single-use up treatment product comprising from about 60% by weight to about 65% by weight of a water-soluble film forming polymeric material, from about 0.01% by weight to about 50% by weight of a moisturizing agent, and from about 0.1% by weight to about 50% by weight of a solidifying agent, wherein said single-use lip treatment product is a film that is capable of substantially dissolving on lips in no more than about 50 seconds and comprises a single layer, wherein said single-use lip treatment product is sized and configured for application to the lips, and wherein the solidifying agent is selected from the group consisting of animal waxes, vegetable waxes, mineral waxes, synthetic waxes, bayberry wax, beeswax $C_{30}$ alkyl dimethicone, candelilla wax, carnauba, ceresin, cetyl esters, esparto, hydrogenated cottonseed oil, hydrogenated microcrystalline wax, hydrogenated rice bran wax, japan wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, solid fatty acid esters, fatty alcohols, fatty acids, copolymers or polymeric blends of ethylene, propylene, butylene, styrene, or vinyl acetate, and combinations thereof.

2. The single-use up treatment product as set forth in claim 1 wherein the water-soluble film forming polymeric material is present in an amount of from about 60% by weight to about 65% by weight.

3. The single-use lip treatment product as set forth in claim 1 wherein the water-soluble film forming polymeric material is selected from the group consisting of starch, pullulan, hydroxypropylmethyl cellulose, hydroxyethyl cellulose, hydroxypropyl cellulose, polyvinyl pyrrolidone, carboxymethylcellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, nigeran, collagen, gelatin, zein, gluten, soy protein isolate, whey protein isolate, casein and mixtures thereof.

4. The single-use lip treatment product as set forth in claim 1 wherein the moisturizing agent is present in an amount of from about 1% by weight to about 25% by weight.

5. The single-use lip treatment product as set forth in claim 1 wherein the moisturizing agent is a humectant-type moisturizing agent selected from the group consisting of N-Acetyl ethanolamine, aloe vera gel, arginine PCA, chitosan PCA, copper PCA, Corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, Urea, Xylitol, and mixtures thereof.

6. The single-use lip treatment product as set forth in claim 5 wherein the humectant-type moisturizing agent is selected from the group consisting of glycerin and sorbitol.

7. The single-use lip treatment product as set forth in claim 1 wherein the moisturizing agent is an occlusive-type moisturizing agent selected from the group consisting of petrolatum, mineral oil, lanolin, lanolin alcohol, tocopherol, esters of tocopherol, alkyl polydimethylsiloxanes, vegetable oils, hydrogenated vegetable oils, fatty acid esters, beeswax, and combinations thereof.

8. The single-use lip treatment product as set forth in claim 7 wherein the occlusive-type moisturizing agent is petrolatum.

9. The single-use lip treatment product as set forth in claim 1 wherein the product has a thickness of from about 15 micrometers to about 80 micrometers.

10. The single-use lip treatment product as set forth in claim 1 wherein the product has a thickness of from about 30 micrometers to about 60 micrometers.

11. The single-use lip treatment product as set forth in claim 1 wherein the product is capable of dissolving on lips in no more than about 20 seconds.

12. The single-use lip treatment product as set forth in claim 1 wherein the product is capable of dissolving on lips in no more than about 15 seconds.

13. The single-use lip treatment product as set forth in claim 1 wherein the product is capable of dissolving on lips in no more than about 10 seconds.

14. The single-use lip treatment product as set forth in claim 1 wherein the product has a length of no more than about 8 centimeters.

15. The single-use lip treatment product as set forth in claim 1 further comprising an additive selected from the group consisting of botanicals, coloring agents, lipids, essential oils, flavorings, pharmaceutically acceptable agents, skin protectants, sunscreens, surfactants, emulsifiers, Vitamin E, and antimicrobials.

16. A dissolvable lip moisturizing product comprising from about 60% by weight to about 65% by weight of pullulan, from about 0.01% by weight to about 50% by weight of glycerin, and from about 0.1% by weight to about 50% by weight of a solidifying agent, wherein said dissolvable lip moisturizing product is sized and configured for application to the lips, wherein said product is capable of dissolving on lips in no more than about 50 seconds, and wherein the solidifying agent is selected from the group consisting of animal waxes, vegetable waxes, mineral waxes, synthetic waxes, bayberry wax, beeswax $C_{30}$ alkyl dimethicone, candelilla wax, carnauba, ceresin, cetyl esters, esparto, hydrogenated cottonseed oil, hydrogenated microcrystalline wax, hydrogenated rice bran wax, japan wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, solid fatty acid esters, fatty alcohols, fatty acids, copolymers or polymeric blends of ethylene, propylene, butylene, styrene, or vinyl acetate, and combinations thereof.

17. The dissolvable lip moisturizing product as set forth in claim 16 wherein the pullulan is present in an amount of from about 60% by weight to about 65% by weight.

18. The dissolvable lip moisturizing product as set forth in claim 16 wherein the glycerin is present in an amount of from about 1% by weight to about 25% by weight.

19. The dissolvable lip moisturizing product as set forth in claim 16 wherein the product has a thickness of from about 15 micrometers to about 80 micrometers.

20. The dissolvable lip moisturizing product as set forth in claim 16 wherein the product has a thickness of from about 30 micrometers to about 60 micrometers.

21. The dissolvable lip moisturizing product as set forth in claim 16 wherein the product is capable of dissolving on lips in no more than about 20 seconds.

22. The dissolvable up moisturizing product as set forth in claim 16 wherein the product is capable of dissolving on lips in no more than about 10 seconds.

23. The dissolvable lip moisturizing product as set forth in claim 16 wherein the product has a length of no more than about 8 centimeters.

24. The dissolvable lip moisturizing product as set forth in claim 16 further comprising an additive selected from the group consisting of botanicals, coloring agents, lipids, essential oils, flavorings, pharmaceutically acceptable agents, skin protectants, sunscreens, surfactants, emulsifiers, Vitamin E, and antimicrobials.

25. A single-use body treatment product comprising from about 40 60% by weight to about 65% by weight of a water-soluble film forming polymeric material, from about 0.01% by weight to about 50% by weight of a moisturizing agent, and from about 0.1% by weight to about 50% by weight of a solidifying agent, wherein said single-use body treatment product is a film and comprises a single layer, and wherein the solidifying agent is selected from the group consisting of animal waxes, vegetable waxes, mineral waxes, synthetic waxes, bayberry wax, beeswax $C_{30}$ alkyl dimethicone, candelilla wax, carnauba, ceresin, cetyl esters, esparto, hydrogenated cottonseed oil, hydrogenated microcrystalline wax, hydrogenated rice bran wax, japan wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, solid fatty acid esters, fatty alcohols, fatty acids, copolymers or polymeric blends of ethylene, propylene, butylene, styrene, or vinyl acetate, and combinations thereof.

26. A single-use lip treatment product comprising from about 60% by weight to about 65% by weight of a water-soluble film forming polymeric material, from about 0.01% by weight to about 50% by weight of a moisturizing agent, and from about 0.1% by weight to about 50% by weight of a solidifying agent, wherein said single-use lip treatment product is a film that is capable of substantially dissolving on lips in no more than about 50 seconds and comprises a single layer, wherein said single-use lip treatment product is sized and configured for application to the lips, and wherein the solidifying agent is selected from the group consisting of bayberry wax, beeswax $C_{30}$ alkyl dimethicone, candelilla wax, carnauba, ceresin, cetyl esters, esparto, hydrogenated cottonseed oil, hydrogenated microcrystalline wax, hydrogenated rice bran wax, japan wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, solid fatty acid esters, fatty alcohols, fatty acids, copolymers or polymeric blends of ethylene, propylene, butylene, styrene, or vinyl acetate, and combinations thereof.

* * * * *

UNITED STATES PATENT AND TRADEMARK OFFICE
CERTIFICATE OF CORRECTION

PATENT NO. : 7,666,396 B2
APPLICATION NO. : 10/659970
DATED : February 23, 2010
INVENTOR(S) : Lange et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1053 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,396 B2 | Page 1 of 1 |
| APPLICATION NO. | : 10/659970 | |
| DATED | : February 23, 2010 | |
| INVENTOR(S) | : Beth A. Lange et al. | |

It is certified that error appears in the above-identified patent and that said Letters Patent is hereby corrected as shown below:

In the Claims

In Claim 1, column 9, line 34, delete "A single-use up treatment" and insert therefor -- A single-use lip treatment --.

In Claim 2, column 9, line 58, delete "The single-use up treatment" and insert therefor -- The single-use lip treatment --.

In Claim 22, column 11, line 35, delete "The dissolvable up moisturizing" and insert therefor -- The dissolvable lip moisturizing --.

In Claim 25, column 12, line 2, delete "about 40 60% by weight" and insert therefor -- about 60% by weight --.

Signed and Sealed this
Fifteenth Day of April, 2014

Michelle K. Lee
*Deputy Director of the United States Patent and Trademark Office*